(12) United States Patent
Zhang et al.

(10) Patent No.: US 11,904,552 B2
(45) Date of Patent: Feb. 20, 2024

(54) PROFILE CONNECTION

(71) Applicant: SAINT-GOBAIN PERFORMANCE PLASTICS CORPORATION, Solon, OH (US)

(72) Inventors: Jianfeng Zhang, Shrewsbury, MA (US); Rachel Z Pytel, Newton, MA (US); Jian L. Ding, Stow, MA (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 81 days.

(21) Appl. No.: 16/918,322

(22) Filed: Jul. 1, 2020

(65) Prior Publication Data

US 2021/0001563 A1    Jan. 7, 2021

Related U.S. Application Data

(60) Provisional application No. 62/936,888, filed on Nov. 18, 2019, provisional application No. 62/869,234, filed on Jul. 1, 2019.

(51) Int. Cl.
| | |
|---|---|
| *F16L 13/02* | (2006.01) |
| *B29C 65/14* | (2006.01) |
| *B29C 65/00* | (2006.01) |
| *A61M 39/00* | (2006.01) |
| *B29K 9/06* | (2006.01) |

(Continued)

(52) U.S. Cl.
CPC ......... *B29C 65/1432* (2013.01); *A61M 39/00* (2013.01); *B29C 66/00143* (2013.01); *B29C 66/71* (2013.01); *B29C 66/73921* (2013.01); *B29C 66/73941* (2013.01); *B29K 2009/06* (2013.01); *B29K 2105/0088* (2013.01); *B29K 2223/06* (2013.01); *B29K 2223/12* (2013.01); *B29L 2023/005* (2013.01);

(Continued)

(58) Field of Classification Search
CPC ..... F16L 31/02; F16L 31/0281; F16L 31/029; F16L 47/00; F16L 47/02; F16L 47/03
USPC ..................... 285/288.1, 288.2, 288.3, 288.4
See application file for complete search history.

(56) References Cited

U.S. PATENT DOCUMENTS

| | | | |
|---|---|---|---|
| 3,597,569 A | 8/1971 | Gerber | |
| 4,039,798 A | 8/1977 | Lythall et al. | |

(Continued)

FOREIGN PATENT DOCUMENTS

| | | |
|---|---|---|
| CA | 2116433 C | 12/2004 |
| CA | 2461223 C | 5/2013 |

(Continued)

OTHER PUBLICATIONS

International Search Report and Written Opinion for PCT/US2020/066066, dated Apr. 7, 2021, 10 pages.

(Continued)

*Primary Examiner* — Aaron M Dunwoody
(74) *Attorney, Agent, or Firm* — Abel Schillinger, LLP; Chi Suk Kim

(57) ABSTRACT

A connection including a first profile having a first end and a first lumen, the first profile including a first polymeric material and a second profile having a second end and a second lumen, the second profile including a second polymeric material, a metal, or combination thereof, wherein the first end and the second end are coincidently welded via an ionized gas treatment.

17 Claims, 1 Drawing Sheet

Figure 1A:
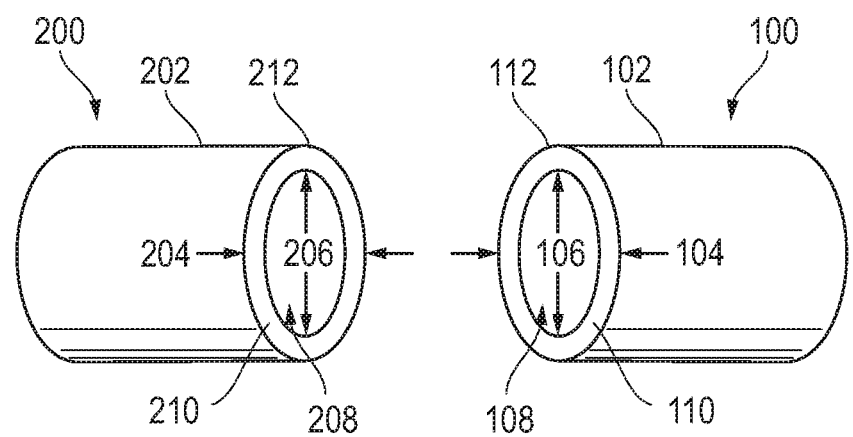

(51) Int. Cl.
    *B29K 105/00* (2006.01)
    *B29K 223/00* (2006.01)
    *B29L 23/00* (2006.01)
    *B32B 15/06* (2006.01)
    *B32B 25/04* (2006.01)

(52) U.S. Cl.
    CPC ............. *B32B 15/06* (2013.01); *B32B 25/042* (2013.01); *F16L 13/02* (2013.01)

(56) References Cited

U.S. PATENT DOCUMENTS

| | | | |
|---|---|---|---|
| 4,516,971 A * | 5/1985 | Spencer | B29C 66/5221 604/905 |
| RE32,056 E | 12/1985 | Granzow et al. | |
| 4,610,670 A | 9/1986 | Spencer | |
| 4,793,880 A | 12/1988 | Shaposka et al. | |
| 4,913,756 A | 4/1990 | Shaposka et al. | |
| 4,987,018 A | 1/1991 | Dickinson et al. | |
| 5,521,351 A | 5/1996 | Mahoney | |
| 5,634,672 A * | 6/1997 | Stack | F16L 59/20 264/269 |
| 5,801,489 A | 9/1998 | Chism, Jr. et al. | |
| 5,858,016 A | 1/1999 | Bacehowski et al. | |
| 6,000,436 A | 12/1999 | Auvil et al. | |
| 6,228,204 B1 | 5/2001 | Reinhardt et al. | |
| 6,270,860 B1 | 8/2001 | Nakata et al. | |
| 6,299,596 B1 | 10/2001 | Ding | |
| 6,468,482 B1 | 10/2002 | Frieze et al. | |
| 6,664,499 B1 | 12/2003 | Brink et al. | |
| 7,226,649 B2 | 6/2007 | Shang et al. | |
| 7,329,608 B2 | 2/2008 | Babayan et al. | |
| 7,442,271 B2 | 10/2008 | Asmussen et al. | |
| 7,754,816 B2 * | 7/2010 | Snider | C08L 23/286 525/212 |
| 8,613,367 B2 | 12/2013 | Ou et al. | |
| 8,975,163 B1 | 3/2015 | Lei et al. | |
| 9,550,015 B2 | 1/2017 | Gray | |
| 10,081,135 B2 | 9/2018 | Patil et al. | |
| 10,195,416 B2 | 2/2019 | Gebauer et al. | |
| 10,550,966 B2 | 2/2020 | Blomberg | |
| 10,794,525 B2 | 10/2020 | Pennock et al. | |
| 11,441,716 B2 | 9/2022 | Tamaribuchi et al. | |
| 2002/0006353 A1 | 1/2002 | Bilstad et al. | |
| 2002/0100540 A1 | 8/2002 | Savitski et al. | |
| 2002/0172780 A1 | 11/2002 | Halverson | |
| 2003/0015816 A1 | 1/2003 | Rapacki et al. | |
| 2003/0102293 A1 | 6/2003 | Therond | |
| 2003/0195609 A1 | 10/2003 | Berenstein et al. | |
| 2003/0196418 A1 | 10/2003 | O'Brien et al. | |
| 2004/0016504 A1 | 1/2004 | Mitarai | |
| 2004/0067705 A1 | 4/2004 | Ton-That et al. | |
| 2004/0144492 A1 | 7/2004 | Ikeda et al. | |
| 2005/0017505 A1 | 1/2005 | Thilly | |
| 2005/0090797 A1 | 4/2005 | Almasian et al. | |
| 2005/0252608 A1 * | 11/2005 | MacDonald | B29C 65/3468 156/273.9 |
| 2006/0070677 A1 | 4/2006 | Inoue et al. | |
| 2006/0081567 A1 | 4/2006 | Dougherty, Sr. et al. | |
| 2006/0110282 A1 | 5/2006 | Bilstad et al. | |
| 2006/0191623 A1 | 8/2006 | Utz et al. | |
| 2006/0284417 A1 * | 12/2006 | Brown | F16L 13/04 285/294.1 |
| 2007/0118225 A1 | 5/2007 | Hestad et al. | |
| 2007/0142960 A1 | 6/2007 | Bollinger et al. | |
| 2008/0009833 A1 | 1/2008 | Corbin et al. | |
| 2008/0202669 A1 | 8/2008 | Zemmouri et al. | |
| 2008/0257604 A1 | 10/2008 | Becker et al. | |
| 2008/0277926 A1 | 11/2008 | Inman, Jr. et al. | |
| 2011/0171480 A1 | 7/2011 | Mori et al. | |
| 2011/0220290 A1 | 9/2011 | Hlavinka et al. | |
| 2013/0158189 A1 | 6/2013 | Reneirs et al. | |
| 2014/0004503 A1 | 1/2014 | Cima et al. | |
| 2014/0077488 A1 | 3/2014 | Wegener et al. | |
| 2014/0197141 A1 | 7/2014 | Dorey et al. | |
| 2014/0263202 A1 | 9/2014 | Partridge | |
| 2014/0283940 A1 | 9/2014 | Bourgeois et al. | |
| 2014/0314818 A1 | 10/2014 | Giare-Patel et al. | |
| 2016/0109052 A1 | 4/2016 | Yodogawa et al. | |
| 2016/0146392 A1 | 5/2016 | Pennock et al. | |
| 2016/0200038 A1 | 7/2016 | Gagne et al. | |
| 2016/0235962 A1 * | 8/2016 | Gebauer | A61M 39/18 |
| 2017/0107345 A1 | 4/2017 | Kon et al. | |
| 2017/0141001 A1 | 5/2017 | Sakiyama et al. | |
| 2017/0221856 A1 | 8/2017 | Yamauchi | |
| 2017/0326584 A1 | 11/2017 | Lennon et al. | |
| 2018/0161554 A1 | 6/2018 | Takemoto | |
| 2018/0320026 A1 | 11/2018 | De Beer | |
| 2019/0048230 A1 | 2/2019 | Hahnel | |
| 2019/0105849 A1 | 4/2019 | Schwalm et al. | |
| 2019/0134243 A1 | 5/2019 | Nelson et al. | |
| 2019/0284443 A1 | 9/2019 | Sherman et al. | |
| 2019/0313863 A1 | 10/2019 | Laundre | |
| 2020/0071199 A1 | 3/2020 | Lewis, III | |
| 2021/0001566 A1 | 1/2021 | Zhang et al. | |
| 2021/0076480 A1 | 3/2021 | Ikedo et al. | |
| 2021/0178506 A1 | 6/2021 | Zhang et al. | |
| 2021/0199226 A1 | 7/2021 | Zhang et al. | |
| 2021/0291291 A1 | 9/2021 | Zhang et al. | |
| 2021/0394459 A1 | 12/2021 | Zhang et al. | |

FOREIGN PATENT DOCUMENTS

| | | |
|---|---|---|
| CN | 1695844 A | 11/2005 |
| CN | 101579757 A | 11/2009 |
| CN | 102061440 A | 5/2011 |
| CN | 102159868 A | 8/2011 |
| CN | 105065804 A | 11/2015 |
| CN | 106795343 A | 5/2017 |
| CN | 206140944 U | 5/2017 |
| CN | 108127239 A | 6/2018 |
| DE | 102011010905 A1 | 8/2012 |
| DE | 102016003862 A | 12/2017 |
| EP | 0064288 A1 | 11/1982 |
| EP | 0479592 A2 | 4/1992 |
| EP | 1445209 B1 | 5/2008 |
| EP | 1656414 B1 | 10/2013 |
| FR | 2793178 A1 | 11/2000 |
| JP | H05456 A | 1/1993 |
| JP | 5042203 A | 2/1993 |
| JP | 6155582 A | 6/1994 |
| JP | 7251456 A | 10/1995 |
| JP | 10861581 A | 3/1996 |
| JP | H0955287 A | 2/1997 |
| JP | H09135881 A | 5/1997 |
| JP | 2000279509 A | 10/2000 |
| JP | 2006124665 A | 5/2006 |
| JP | 2009028922 A | 2/2009 |
| JP | 2013132822 A | 7/2013 |
| JP | 2018015904 A | 2/2018 |
| JP | 2019052716 A | 4/2019 |
| KR | 20030043478 A | 6/2003 |
| KR | 20150054280 A | 5/2015 |
| KR | 101708024 B1 | 2/2017 |
| KR | 20190117741 A | 10/2019 |
| TW | 201510402 A | 3/2015 |
| WO | 2015075040 A1 | 5/2015 |
| WO | 2018146880 A1 | 8/2018 |
| WO | 2019130223 A1 | 7/2019 |
| WO | 2021003243 A1 | 1/2021 |
| WO | 2021118780 A1 | 6/2021 |
| WO | 2021133677 A1 | 7/2021 |
| WO | 2021188261 A1 | 9/2021 |

OTHER PUBLICATIONS

International Search Report and Written Opinion for PCT/US2021/037442, dated Oct. 7, 2021, 9 pages.

International Search Report and Written Opinion for PCT/US2020/040455, dated Oct. 22, 2020, 10 pages.

International Search Report and Written Opinion for PCT/US2020/040454, dated Oct. 15, 2020, 11 pages.

(56) References Cited

OTHER PUBLICATIONS

International Search Report and Written Opinion for PCT US2020/061198, dated Mar. 12, 2021, 9 pages.

Kinney, Shawn D. et al., Thermoplastic Tubing Welders and Sealers: Forging the Future of Disposable Technologies in the Biopharmaceutical Industry, BioProcess International, May 2007, pp. 52-61.

TSCD-Q Sterile Tubing Welder, Discover Polyurethane Tubing Connections based on Proven Terumo BCT Technology, Terumo BCT, Inc., 2014, 6 pages.

SCD IIB, Sterile Tubing Welder, Experience Fast, Easy, Reliable Welds, Terumo BCT, Inc., 2014, 6 pages.

CPC, Comparison Guide: Tube Welders and Aseptic Connectors, Technical Guide 7009, Colder Products Company, 2018, 3 pages.

Annunziata, Marco et al., "Bacterial inactivation/sterilization by argon plasma treatment on contaminated titanium implant surfaces: In vitro study ," Med Oral Patol Oral Cir Bucal. (2015), doi:10.4317/medoral.20845, 4 pages.

International Search Report and Written Opinion for PCT/US2021/019197, mailed Jun. 11, 2021, 9 pages (Atty Docket No. 19-OF-0437WO01).

CJan Fluid Technology, 2017, "The Differences Between Silicone and PVC", https://web.archive.org/web/20170922114948/http://www.cjanfluid.com/blog/the-differences-between-silicone-and-pvs.html, 3 pages.

Ageorges et al., "Advances in fusion bonding techniques for joining thermoplastic matrix composites: a review", dated Oct. 25, 2000, Composites: Part A, 32, Elsevier.com, pp. 839-857 (Year: 2000).

Masuzawa et al., "Ultrasonic Welding of Plastic Pipes Using Torsional Vibration", Japanese Journal of Applied Physics, vol. 37, Part 1, No. 5B, pp. 3007-3008 (Year: 1997).

PVC Pipe Industry News, "Top 10 Benefits of PVC Pipes", dated Jan. 30, 2015, <https://www.thinkpipesthinkpvc.com.au/about-us/latest-news/entry/top-10-benefits-of-pvc-pipes>, pp. 1-4 (Year: 2015).

Medical Design Briefs, "Why is Silicone the Material of Choice for Healcare Tubing?", dated Nov. 1, 2018, <https://www.medicaldesignbriefs.com/component/content/article/mdb/pub/features/articles/33244>, pp. 1-7, (Year: 2018).

* cited by examiner

PROFILE CONNECTION

CROSS-REFERENCE TO RELATED APPLICATION(S)

This application claims priority under 35 U.S.C. § 119(e) to U.S. Provisional Patent Application No. 62/869,234, entitled "PROFILE CONNECTION", by Jianfeng ZHANG, Rachel Z. PYTEL, and Jian L. DING, filed Jul. 1, 2019, and this application claims priority under 35 U.S.C. § 119(e) to U.S. Provisional Patent Application No. 62/936,888, entitled "PROFILE CONNECTION," by Jianfeng ZHANG, Rachel Z. PYTEL, and Jian L. DING, filed Nov. 18, 2019, both of which are assigned to the current assignee hereof and incorporated herein by reference in their entireties.

FIELD OF THE DISCLOSURE

The disclosure, generally, is related to a connection and a method providing a sterile connection.

BACKGROUND

Many industries utilize sterile connections for the delivery and removal of fluids. Since sterile connections may be used in a variety of industries, such as the medical industry and pharmaceutical industry, thermoplastic and thermoset elastomers are typically used that are non-toxic, flexible, thermally stable, have low chemical reactivity, and can be produced in a variety of sizes. In many instances, it is desirable to connect two different profiles to create a sterile fluid connection. Unfortunately, it is difficult to effectively provide a weld with a thermoset elastomeric material and in many cases, two different materials, such as two different polymeric materials. For instance, a silicone elastomer is a thermoset material that cannot be melted and thus, cannot be welded with conventional high temperature methods. Further, it is a challenge to maintain any sterility, especially when welding two profiles.

Accordingly, an improved sterile connection and method of providing a weld between two profiles is desired.

SUMMARY

In an embodiment, a connection includes a first profile having a first end and a first lumen, the first profile including a first polymeric material and a second profile having a second end and a second lumen, the second profile comprising a second polymeric material, a metal, or combination thereof, wherein the first end and the second end are coincidently welded via an ionized gas treatment.

In another embodiment, a sterile connection includes a first profile having a first end and a first lumen, the first profile including a first polymeric material and a second profile having a second end and a second lumen, the second profile including a second polymeric material, a metal, or combination thereof, wherein the first end and the second end are coincidently welded via an ionized gas treatment, wherein the ionized gas treatment provides a sterile connection between the first profile and the second profile.

In yet another embodiment, a method of providing a sterile connection includes:
providing a first profile having a first end and a first lumen, the first profile including a first polymeric material; providing a second profile having a second end and a second lumen, the second profile including a second polymeric material, a metal, or combination thereof; providing an ionized gas treatment; and contacting the first end directly to the second end to coincidently weld the first end to the second end and provide a sterile connection between a treated surface of the first profile and a treated surface of the second profile.

BRIEF DESCRIPTION OF THE DRAWING(S)

The present disclosure may be better understood, and its numerous features and advantages made apparent to those skilled in the art by referencing the accompanying drawings.

Figure 1B:
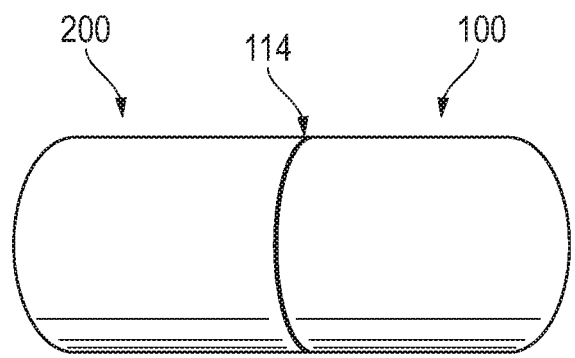

FIGS. 1A and 1B include illustrations of exemplary sterile connections.

The use of the same reference symbols in different drawings indicates similar or identical items.

DETAILED DESCRIPTION

The following description in combination with the figures is provided to assist in understanding the teachings disclosed herein. The following discussion focuses on specific implementations and embodiments of the teachings. This focus is provided to assist in describing the teachings and should not be interpreted as a limitation on the scope or applicability of the teachings.

As used herein, the terms "comprises", "comprising", "includes", "including", "has", "having", or any other variation thereof, are open-ended terms and should be interpreted to mean "including, but not limited to . . . ." These terms encompass the more restrictive terms "consisting essentially of" and "consisting of." In an embodiment, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in reference books and other sources within the structural arts and corresponding manufacturing arts. Unless indicated otherwise, all measurements are at about 25° C. For instance, values for viscosity are at 25° C., unless indicated otherwise.

The disclosure generally relates to a connection. The connection includes a first profile having a first end and a first lumen, the first profile including a first polymeric material. The sterile connection includes second profile having a second end and a second lumen, the second profile including a second polymeric material, a metal, or combination thereof. A connection is provided by coincidentally welding the first end of the first lumen with the second end of the second lumen via an ionized gas treatment. The ionized gas treatment welds the first end of the first profile to the second end of the second profile when they are placed in direct contact at an interface to provide an effective seal between the two profiles. For instance, the coincident weld withstands a seal integrity pressure test of at least 1 psi, such as at least 5 psi, such as at least 10 psi, such as at least 15 psi, or even at least 20 psi air pressure for about 30 minutes under dry and wet conditions, as described further in the Examples. In an embodiment, the ionized gas treatment provides sterility to the surface it treats, i.e. sterilizes the treated surface. In an embodiment, "providing sterility" includes maintaining sterility for a pre-sterilized first profile and/or a pre-sterilized second profile. In a particular embodiment, the ionized gas treatment provides a sterile connection between the first profile and the second profile, such as between a treated surface of the first profile and a treated surface of the second profile.

Any profile is envisioned to provide a fluid connection between two lumens for fluid to flow through and between the first profile and the second profile. For instance, the profile is any connector, a tube, a port, a hose, a nozzle, a needle, and the like. The first profile and the second profile may be the same or different. In an embodiment, the first profile and the second profile are both tubes. In another embodiment, the first profile is a tube and the second profile is a port. In an example, the first profile and/or the second profile may be a single homogenous polymeric material. In an embodiment, the first profile and/or the second profile may be a multi-layered composite material, for example, including more than one distinct polymeric layer.

In an embodiment, the first profile includes a first polymeric material. Any polymeric material is envisioned. In an embodiment, the first polymeric material includes a thermoplastic elastomer, a thermoset elastomer, or combination thereof. In a particular embodiment, the first polymeric material is a thermoplastic elastomer and includes a polystyrene, a polyester, a silicone copolymer, silicone thermoplastic vulcanizate, a copolyester, a polyamide, a fluoropolymer, a polyolefin, a polyether-ester copolymer, a thermoplastic urethane, a polyether amide block (PEBA) copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or combination thereof. In an embodiment, the first polymeric material includes a styrene block copolymer blended with a polyolefin, such as a polypropylene.

In an embodiment, the first polymeric material is a fluoropolymer. An exemplary fluoropolymer includes a copolymer of a poly vinylidene fluoride (PVDF) and a hexafluoropropylene (HFP), a polytetrafluoroethylene (PTFE), a fluorinated ethylene propylene copolymer (FEP), a copolymer of tetrafluoroethylene and perfluoropropyl vinyl ether (PFA), a copolymer of tetrafluoroethylene and perfluoromethyl vinyl ether (MFA), a copolymer of ethylene and tetrafluoroethylene (ETFE), a copolymer of ethylene and chlorotrifluoroethylene (ECTFE), a polychlorotrifluoroethylene (PCTFE), a poly vinylidene fluoride (PVDF), a terpolymer including a tetrafluoroethylene, a hexafluoropropylene, and a vinylidenefluoride (THV), a polyvinyl fluoride (PVF, e.g., Tedlar™), a terpolymer of tetrafluoroethylene, hexafluoroproplyene, and ethylene, any blend, any alloy, or combination thereof.

In a particular embodiment, the first polymeric material includes a polyolefin. A typical polyolefin may include a homopolymer, a copolymer, a terpolymer, an alloy, or any combination thereof formed from a monomer, such as ethylene, propylene, butene, pentene, methyl pentene, octene, or any combination thereof. An exemplary polyolefin includes a polyethylene, high density polyethylene (HDPE), medium density polyethylene (MDPE), low density polyethylene (LDPE), ultra or very low density polyethylene (VLDPE), ethylene propylene copolymer, ethylene butene copolymer, polypropylene (PP), polybutene, polybutylene, polypentene, polymethylpentene, polystyrene, ethylene propylene rubber (EPR), ethylene octene copolymer, blend thereof, mixture thereof, and the like. The polyolefin further includes olefin-based random copolymers, olefin-based impact copolymers, olefin-based block copolymers, olefin-based specialty elastomers, olefin-based specialty plastomers, blends thereof, mixture thereof, and the like. In an example, the polyolefin includes polyethylene. In an example, the polyolefin includes polypropylene. In a particular example, the polyolefin is a random propylene copolymer. In an embodiment, the polyolefin is a gamma stabilized polypropylene.

In an additional example, the first polymeric material may include a styrene block copolymer that includes, for example, a multiblock copolymer such as a diblock, triblock, polyblock, or any combination thereof. In a particular embodiment, the styrene block copolymer is a block copolymer having AB units. Typically, the A units are alkenyl arenes such as a styrene, an alpha-methylstyrene, para-methylstyrene, para-butyl styrene, or combination thereof. In a particular embodiment, the A units are styrene. In an embodiment, the B units include alkenes such as butadiene, isoprene, ethylene, butylene, propylene, or combination thereof. In a particular embodiment, the B units are ethylene, isoprene, or combinations thereof. Exemplary styrene block copolymers include triblock styrenic block copolymers (SBC) such as styrene-butadiene-styrene (SBS), styrene-isoprene-styrene (SIS), styrene-ethylene butylene-styrene (SEBS), styrene-ethylene propylene-styrene (SEPS), styrene-ethylene-ethylene-butadiene-styrene (SEEBS), styrene-ethylene-ethylene-propylene-styrene (SEEPS), styrene-isoprene-butadiene-styrene (SIBS), or combination thereof. In an embodiment, the styrene block copolymer is saturated, i.e. does not contain any free olefinic double bonds. In an embodiment, the styrene block copolymer contains at least one free olefinic double bond, i.e. an unsaturated double bond. In a particular embodiment, the styrene block copolymer is a styrene-ethylene based copolymer, a styrene isoprene based copolymer, a blend, or combination thereof.

In an embodiment, the first polymeric material is a thermoset elastomer. Any thermoset elastomer is envisioned. In a particular embodiment, the thermoset elastomer includes a silicone elastomer, a dine elastomer, a butyl rubber, a natural rubber, a polyurethane rubber, an ethylene propylene diene monomer rubber, an isoprene rubber, a nitrile rubber, a styrene butadiene rubber, a blend, or combination thereof. Any rubber for medical/pharmaceutical applications is envisioned. In a particular embodiment, the first polymeric material includes a silicone elastomer.

A typical silicone elastomer includes a silicone matrix component. An exemplary silicone matrix component includes a polyorganosiloxane. Polyorganosiloxanes include a polyalkylsiloxane, a polyarylsiloxane, or combination thereof. Any reasonable polyalkylsiloxane is envisioned. Polyalkylsiloxanes include, for example, silicone polymers formed of a precursor, such as dimethylsiloxane, diethylsiloxane, dipropylsiloxane, methylethylsiloxane, methylpropylsiloxane, or combinations thereof. In a particular embodiment, the polyalkylsiloxane includes a polydialkylsiloxane, such as polydimethylsiloxane (PDMS). In a particular embodiment, the polyalkylsiloxane is a silicone hydride-containing polyalkylsiloxane, such as a silicone hydride-containing polydimethylsiloxane. In a further embodiment, the polyalkylsiloxane is a vinyl-containing polyalkylsiloxane, such as a vinyl-containing polydimethylsiloxane. The vinyl group may be an endblock of the polyalkylsiloxane, on chain of the polyalkylsiloxane, or any combination thereof. In yet another embodiment, the silicone matrix component is a combination of a hydride-containing polyalkylsiloxane and a vinyl-containing polyalkylsiloxane.

In an embodiment, the first polymeric material is a thermoset elastomer and more particularly, a diene elastomer. The diene elastomer may be a copolymer formed from at least one diene monomer. For example, the diene elastomer may be a copolymer of ethylene, propylene and diene monomer (EPDM), a thermoplastic EPDM composite, or combination thereof. An exemplary diene monomer may include a conjugated diene, such as butadiene, isoprene, chloroprene, or the like; a non-conjugated diene including from 5 to about 25 carbon atoms, such as 1,4-pentadiene, 1,4-hexadiene, 1,5-hexadiene, 2,5-dimethyl-1,5-hexadiene, 1,4-octadiene, or the like; a cyclic diene, such as cyclopentadiene, cyclohexadiene, cyclooctadiene, dicyclopentadiene, or the like; a vinyl cyclic ene, such as 1-vinyl-1-cyclopentene, 1-vinyl-1-cyclohexene, or the like; an alkylbicyclononadiene, such as 3-methylbicyclo-(4,2,1)-nona-3,7-diene, or the like; an indene, such as methyl tetrahydroindene, or the like; an alkenyl norbornene, such as 5-ethylidene-2-norbornene, 5-butylidene-2-norbornene, 2-methallyl-5-norbornene, 2-isopropenyl-5-norbornene, 5-(1,5-hexadienyl)-2-norbornene, 5-(3,7-octadienyl)-2-norbornene, or the like; a tricyclodiene, such as 3-methyltricyclo $(5,2,1,0^2,6)$-deca-3,8-diene or the like; or any combination thereof.

Depending on the composition of the first polymeric material, the first polymeric material may be formed with any reasonable component such as any precursor with the addition of any reasonable additive. An additional additive includes, but is not limited to, a catalyst, a filler, a plasticizer, a lubricant, an antioxidant, a colorant, an optically transparent conductive additive, an adhesion promoter, heat stabilizer, acid scavenger, UV stabilizer, processing aid, or combination thereof. In a particular embodiment, the precursor, the additional additive such as the catalyst, the filler, plasticizer, lubricant, antioxidant, colorant, an optically transparent conductive additive, an adhesion promoter, heat stabilizer, acid scavenger, UV stabilizer, processing aid, or combination thereof are dependent upon the first polymeric material chosen and final properties desired for the first profile.

Any reasonable catalyst that can initiate crosslinking of the polymeric material is envisioned. Exemplary catalysts include a catalyst that may be heat cured, IR radiation cured, e-beam cured, or combination thereof. The catalyst is dependent upon the polymeric material chosen. The catalyst may or may not be used in combination with a crosslinker promoter, such as triallyl cyanurate (TAC), triallyl isocyanurate (TAIL), or combination thereof. In an embodiment, the additive includes any reasonable adhesion promoter. Any reasonable adhesion promoter that promotes adhesion of adjacent layers is envisioned and is dependent upon the adjacent layers. Exemplary lubricants include silicone oil, waxes, slip aids, antiblock agents, the like, or any combination thereof. Exemplary lubricants further include silicone grafted polyolefin, polyethylene or polypropylene waxes, Oleic acid amide, erucamide, stearate, fatty acid esters, the like, or any combination thereof. Exemplary antioxidants include phenolic, hindered amine antioxidants. Exemplary fillers include calcium carbonate, talc, radio-opaque fillers such as barium sulfate, bismuth oxychloride, any combinations thereof, and the like. In an embodiment, the filler includes a functionalized filler. Exemplary functionalized fillers include, for example, a base filler that has a functional moiety that forms a chemical bond with the second polymeric material. Any reasonable base filler is envisioned such as a silica filler, fumed silica filler, quartz, glass filler, aluminum (AlO(OH)), alumino-silicate, inorganic oxides, resinous filler, carbon black, graphite, graphene, carbon nanotube (CNT), fullerene or combination thereof. In a particular embodiment, the functionalized filler includes a silica filler. Any functional moiety is envisioned that has an adhesive affinity to the second polymeric material. The functionalized moiety is, for example, a silane attached to the base filler, wherein the silane includes an acryl functional group, an epoxy functional group, a chloro functional group, or combination thereof. In an embodiment, any reasonable silane is envisioned and includes, for example, an alkoxysilane such as a trimethoxysilane, a triethoxysilane, or combination thereof. In an embodiment, the functionalized filler is a silicone-hydride attached to the base filler. In a particular embodiment, the silicone-hydride is trimethylsiloxy-terminated. When present as the functional moiety, any reasonable amount of functionalized filler is envisioned to provide an increased adhesive bond between the first polymeric material and the second polymeric material. In an embodiment, the functionalized filler forms a cohesive bond between the first polymeric material and the second polymeric, i.e. cohesive failure occurs wherein the structural integrity of the first profile and/or the second profile fails before the bond between the two materials fails. In an exemplary embodiment, the functionalized filler is mixed with the polymeric material to form a homogenous mixture of the functionalized filler contained with a matrix of the polymeric material. In an embodiment, the functionalized filler may or may not form a reactive and covalent bond with the polymeric material. In a more particular embodiment, the functionalized filler does not form a reactive and covalent bond with the polymeric material. Exemplary plasticizers include any known plasticizers such as a citrate, a phthalate, a trimellitate, 1,2-cyclohexane dicarboxylic acid diisonoyl ester (DINCH), an adipate, a polymeric plasticizer, a castor oil, a caster oil derivative, mineral oils, soybean oil, such as epoxidized soybean oil, the like, or any combination thereof.

Typically, the additional additive may be present at an amount of not greater than about 70% by weight of the total weight of the polymeric material, such as not greater than about 60% by weight of the total weight of the polymeric material, such as not greater than about 50% by weight of the total weight of the polymeric material, such as not greater than about 40% by weight of the total weight of the polymeric material, or even not greater than about 30% by weight of the total weight of the polymeric material. In an alternative embodiment, the polymeric material may be substantially free of an additional additive such as a catalyst, lubricant, a filler, a plasticizer, an antioxidant, a colorant, an adhesion promoter, heat stabilizer, acid scavenger, UV stabilizer, processing aid, or combination thereof. "Substantially free" as used herein refers to less than about 1.0% by weight, or even less than about 0.1% by weight of the total weight of the polymeric material.

Further included is a second profile. The second profile includes a second polymeric material, a metal, or combination thereof. In an embodiment, the second polymeric material includes a thermoplastic elastomer, a thermoset elastomer, or combination thereof as described for the first polymeric material. In an embodiment, the first polymeric material and the second polymeric material are the same polymeric material. In another embodiment, the first polymeric material and the second polymeric material are different polymeric materials. For instance, the connection may be between any combination of the first polymeric material and the second polymeric material being: a silicone elastomer, a styrene block copolymer, a polyvinyl chloride, a fluoropolymer, a polyolefin, a polycarbonate, a diene copolymer, a blend, or combination thereof. In an embodiment, the first polymeric material and/or the second polymeric material include a silicone elastomer, a styrene block copolymer blended with a polyolefin, a polyvinyl chloride, a polytetrafluoroethylene (PTFE), a fluorinated ethylene propylene copolymer (FEP), a copolymer of tetrafluoroethylene and perfluoropropyl vinyl ether (PFA), a polyethylene, a polycarbonate, a polyolefin, a diene copolymer, a blend, or combination thereof. In an embodiment, the first polymeric material and/or the second polymeric material are a silicone elastomer, a styrene block copolymer blended with a polyolefin, or combination thereof. In an embodiment, the second profile includes a metal. Any metal is envisioned. In a particular embodiment, the second profile is a stainless steel.

FIG. 1A is a view of a first profile 100 and a second profile 200 according to an embodiment. Typically, the first profile 100 and the second profile 200 is any commercially available profile. In a particular embodiment, the first profile 100 is in the form of a tube including a body 102 having an outside diameter 104 and an inner diameter 106. The inner diameter 106 can form a hollow bore 108 of the body 102. The hollow bore 108 defines a central lumen of the tube for fluid flowthrough. In addition, the body 102 is illustrated as a single layer, the single layer including the first polymeric material. The body 102 can include a wall thickness 110 that is measured by the difference between the outside diameter 104 and the inner diameter 106.

In a particular embodiment, the outside diameter 104 of the body 102 is about 0.025 inches to about 5.0 inches, such as about 0.15 inches to about 2.0 inches. It will be appreciated that the outside diameter 104 can be within a range between any of the minimum and maximum values noted above. In an embodiment, the inner diameter 106 of the body 102 is about 0.005 inches to about 4.0 inches, such as about 0.06 inches to about 1.0 inches. It will be appreciated that the inner diameter 106 can be within a range between any of the minimum and maximum values noted above. The wall thickness 110 is about 0.02 inches to about 4.0 inches, such as about 0.05 inches to about 1.0 inch, or even about 0.1 inches to about 0.375 inches. It will be appreciated that the wall thickness 110 can be within a range between any of the minimum and maximum values noted above. Further, the body 102 has a first end 112.

Although the cross-section of the inner bore 108 perpendicular to an axial direction of the body 102 in the illustrative embodiment shown in FIG. 1A has a circular shape, the cross-section of the inner bore 108 perpendicular to the axial direction of the body 102 can have any cross-section shape envisioned.

In a particular embodiment, the second profile 200 is in the form of a tube and can include a body 202 having an outside diameter 204 and an inner diameter 206. The inner diameter 206 can form a hollow bore 208 of the body 202. The hollow bore 208 defines a central lumen of the tube for fluid flowthrough. In addition, the body 202 is illustrated as a single layer, the single layer including the second polymeric material. The body 202 can include a wall thickness 210 that is measured by the difference between the outside diameter 204 and the inner diameter 206.

In a particular embodiment, the outside diameter 204 of the body 102 is about 0.025 inches to about 5.0 inches, such as about 0.15 inches to about 2.0 inches. It will be appreciated that the outside diameter 204 can be within a range between any of the minimum and maximum values noted above. In an embodiment, the inner diameter 206 of the body 202 is about 0.005 inches to about 4.0 inches, such as about 0.06 inches to about 1.0 inches. It will be appreciated that the inner diameter 206 can be within a range between any of the minimum and maximum values noted above. The wall thickness 210 is about 0.02 inches to about 4.0 inches, such as about 0.05 inches to about 1.0 inch, or even about 0.1 inches to about 0.375 inches. It will be appreciated that the wall thickness 210 can be within a range between any of the minimum and maximum values noted above. Further, the body 202 has a second end 212.

Although the cross-section of the inner bore 208 perpendicular to an axial direction of the body 202 in the illustrative embodiment shown in FIG. 1A has a circular shape, the cross-section of the inner bore 208 perpendicular to the axial direction of the body 202 can have any cross-section shape envisioned.

Although illustrated as a single layer tube for both the first profile 100 and the second profile 200, any number of layers is envisioned. For instance, the first profile and the second profile include one layer, two layers, three layers, or even a greater number of layers. Further, although illustrated as both tubes with substantially the same inner diameter, outer diameter, and wall thickness, the first profile 100 and the second profile 200 can have the same or different configurations. Irrespective of the number of layers present, the outside diameter and inner diameter of the first profile 100 and the second profile 200 can have any values as defined for the single layer tubes 100, 200 defined in FIG. 1A. The number of layers is dependent upon the final properties desired for the sterile connection. Further, although illustrated as a single lumen, i.e. hollow bore 108 and 208 for both the first profile 100 and the second profile 200, any number of lumen is envisioned. For instance, the first profile and/or the second profile include a plurality of lumen.

In an embodiment, the first profile 100, the second profile, 200, or combination thereof may further include other layers. Other layers include, for example, a polymeric layer, a reinforcing layer, an adhesive layer, a barrier layer, a chemically resistant layer, a metal layer, any combination thereof, and the like. Any additional layer is envisioned and is dependent upon the material chosen. In an embodiment, any number of polymeric layers is envisioned.

In an embodiment, a method of providing a connection is provided. The method includes providing the first profile 100 having the first end 112 and the first lumen 108. The method further includes providing the second profile 200 having the second end 212 and the second lumen 208. In an embodiment, at least the first profile 100, the second profile 200, or combination thereof is cut. In a particular embodiment, the first end 112 and the second end 212 are coincidently welded together via an ionized gas treatment, the interface of the coincidental weld having an exterior seam 114. For instance, the ionized gas treatment is provided to treat a surface of the first end 112 and a surface of the second end 212 and the first end 112 and the second end 212 are placed in direct contact to coincidentally weld the first end 112 to the second end 212. Typically, a compression force of less than 100 Newtons (N) is applied to the abutting first end 112 and second end 212. In a particular embodiment, the first end 112 has a cross-section across the wall thickness 110 that is in full and direct contact with a cross-section across the wall thickness 210 of the second end 112. In a particular embodiment, the first profile 100, the second profile 200, or combination thereof has a desirable surface roughness to provide a desirable seal. For instance, the cross-section across the wall thickness 110 of the first profile 100, the cross-section across the wall thickness 210 of the second profile, or combination thereof has a Ra of less than about 20 µm, such as less than about 5 µm, such as less than about 1 µm, or even less than about 0.5 µm, as measured by a MarSurf M 300C Mobile Roughness Measuring Instrument.

The interface has further advantageous physical and chemical properties. In an embodiment, the interface has a mechanical strength of at least 2%, at least 10%, or even at least 35% of a bulk material of the first profile and the second profile, testing conditions as described by the tensile test in the Examples. For instance, the interface has a failure mode of adhesive failure, or even cohesive failure. Although not being bound by theory, the ionized gas treatment at least excites an atom at a molecular level to provide the coincident weld. For instance, the interface has an oxygen atomic concentration of greater than about 2%, such as greater than about 5%, such as greater than about 10%, or even greater than about 15%, compared to a bulk material of the first profile and a bulk material of the second profile via XPS. For instance, the interface has a nitrogen atomic concentration of greater than about 2%, such as greater than about 5%, such as greater than about 10%, or even greater than about 15%, compared to a bulk material of the first profile and a bulk material of the second profile via XPS. In a particular embodiment, the interface has a higher valence of an element, compared to a bulk material of the first profile and a bulk material of the second profile. Further, a surface tension at the interface is greater than about 20 mN/m (milliNewton per meter), such as greater than about 22 mN/m, or even greater than about 25 mN/m, as described by the surface energy test in the Examples. For instance, the treated surface has a surface tension of greater than about 20 mN/m, such as greater than about 22 mN/m, or even greater than about 25 mN/m. In particular, a surface tension is increased at a treated interface for connection and/or treated surface for at least about 1 mM/m, at least about 3 mM/m, or even at least than about 10 mM/m, as described by the surface energy test in the Examples.

In an embodiment, the coincidental weld 114 is a circumferential seal wherein the welded ends, 112 and 212, are abutted to maintain fluid flow through the hollow bore 108 and 208. The coincident weld provides an advantageous seal between the first profile 100 and the second profile 200. For instance, the coincident weld withstands a seal integrity pressure test of at least 1 psi, such as at least 5 psi, such as at least 10 psi, such as at least 15 psi, or even at least 20 psi air pressure for about 30 minutes under dry and wet conditions, as described in the Examples.

Typically, the interface is substantially free of a bonding material. Any bonding material includes any external adhesive material envisioned such as any added material that provides adhesive properties. Furthermore, the interface is substantially free of any reversible chemistry, such as dynamic covalent chemistry. "Dynamic covalent chemistry" as used herein refers to a chemical reaction that forms a new chemical compound that is different than an original chemical compound. Exemplary chemical reactions include an Aldol reaction, a Diels-Alder reaction, imine formation, aminal formation, and disulfide exchange. Furthermore, the ionized gas treatment does not increase a temperature of a treated bulk to exceed the degradation temperature of the bulk material.

In a particular embodiment, a sterile connection is provided between the first profile 100 and the second profile 200. In an embodiment, at least the first profile 100, the second profile 200, or combination thereof are sterile prior to the coincident weld. In an embodiment, the ionized gas treatment provides a sterile connection between the first profile 100 and the second profile 200 or at least maintains sterility of a pre-sterilized first profile 100 and/or a pre-sterilized second profile 200. In an embodiment, the ionized gas treatment provides a sterile connection between the treated surface of the first profile 100 and the treated surface of the second profile 200 or at least maintains sterility of a treated surface of a pre-sterilized first profile 100 and/or a treated surface of a pre-sterilized second profile 200. In an embodiment, the ionized gas treatment sterilizes the treated surface of the first profile 100, the treated surface of the second profile 200, or combination thereof. Although not illustrated, the ionized gas treatment may be used to provide a visible difference at the interface on a treated and/or bonded area versus non-treated and/or non-bonded area. The visible difference may be advantageous as a visual indicator that a seal has been achieved or when the seal is no longer present.

An ionized gas treatment includes, for example, corona treatment, plasma treatment, ion treatment, or combination thereof. For instance, the corona treatment ionizes the atmosphere to activate a surface of the first profile and the second profile. In an embodiment, the ionized gas treatment includes plasma treatment which ionizes a gas such as oxygen, argon, nitrogen, compressed air, or combination thereof. Any conditions of the ionized gas treatment are envisioned that provides a weld as well as sterile conditions for the first profile 100 and the second profile 200. For instance, the plasma treatment is provided for less than 2 minutes, such as less than 1 minute, such as less than 45 seconds, such as less than 30 seconds, or even less than 10 seconds. In a particular embodiment, an extraction profile of the first profile and the second profile before and after ionized gas treatment is substantially identical, indicating that the chemical composition of the first profile and the second profile has not changed before and after ionized gas treatment. Furthermore, a change in particulates in the first profile and the second profile before and after ionized gas treatment is +/−5%, such as +/−15%, or even +/−50%. In an embodiment, the profiles may be surface treated multiple times. For instance, the method can include disconnecting the coincident weld at the interface, providing an additional ionized gas treatment, and contacting the first end directly to the second end to coincidently bond the first end to the second end at the interface.

Since the ionized gas provides sterility to the first profile 100 and the second profile 200, a further sterilization process is not required. Further, the ionized gas treatment provides an effective seal where the coincidental weld is substantially free of an adhesive, a primer, a chemical treatment, or combination thereof. Any energy, dependent on power and time, is envisioned that activates the surface of the first profile and the second profile. For examples, a power output is about 480 Watts for about 5 seconds.

In an embodiment, a reinforcement (not illustrated) can be used to reinforce the exterior seam 114. In an embodiment, the reinforcement is a fastening device that surrounds at least a portion of the exterior seam of the coincidental weld. In a particular embodiment, the fastening device that surrounds the entire exterior seam of the coincidental weld. Any fastening device is envisioned such as, for example, a clamp, a polymer tape, an overmolded polymer, a glue, or combination thereof. In a particular embodiment, the fastening device is a polymer tape such as a silicone tape. The silicone tape may be self-adhesive. In another embodiment, a surface between the polymer tape is surface treated to enhance the adhesion of the polymer tape to an exterior surface adjacent to the coincidental weld. For instance, the surface of the polymer tape is treated. In another embodiment, the outer surface of the exterior seam is treated. In a particular embodiment the surface between the polymer tape is surface treated with the ionized gas treatment described for the welding and sterilizing of the first profile and the second profile. Any sequence of surface treating the polymer tape concurrently or subsequently with surface treatment with the ionized gas treatment for welding is envisioned.

In exemplary embodiments, the first profile and the second profile with the coincidental weld can be used in a variety of applications where a welded connection is desired. In a particular embodiment, a sterile connection is achieved. Advantageously and in a particular embodiment, the ionized gas treatment provides a method of welding and sterilizing a multitude of polymeric materials not yet before welded while maintaining a sterilized connection. In particular, the sterile nature of the coincidental weld is useful for any application where sterility is desired. For instance, the coincidental weld of any profiles has potential for FDA, ADCF, USP Class VI, NSF, European Pharmacopoeia compliant, United States Pharmacopoeia (USP) compliant, USP physiochemical compliant, Japanese Pharmacopeia, ISO 10993 Standard for evaluating biocompatibility of a medical device, and other regulatory approvals. In a particular embodiment, the profile is non-cytotoxic, non-hemolytic, non-pyrogenic, animal-derived component-free, non-mutagenic, non-bacteriostatic, non-fungistatic, or any combination thereof.

In an embodiment, the method of providing a sterile connection may be used in applications such as industrial, medical applications, health care, biopharmaceutical, drinking water, food & beverage applications, dairy applications, laboratory applications, FDA applications, and the like. In an exemplary embodiment, the method of providing a sterile connection may be used in applications such as a fluid transfer tube in food and beverage processing equipment, a fluid transfer tube in medical and health care, biopharmaceutical manufacturing equipment, and peristaltic pump tube for medical, laboratory, and biopharmaceutical applications.

In a particular embodiment, a fluid source, such as a container, reactor, reservoir, tank, or bag, is coupled to the first profile and/or the second profile. The first profile and/or the second profile may engage a pump, fitting, valve, dispenser, or another container, reactor, reservoir, tank, or bag. In an example, the first profile and/or the second profile may be coupled to a water container and may have a dispenser fitting. In another example, the first profile and/or the second profile may be coupled to a fluid bag and coupled to a valve. In a further example, the profile may be coupled to a container, be engaged in a pump, and be coupled to a second container.

Many different aspects and embodiments are possible. Some of those aspects and embodiments are described herein. After reading this specification, skilled artisans will appreciate that those aspects and embodiments are only illustrative and do not limit the scope of the present invention. Embodiments may be in accordance with any one or more of the items as listed below.

Embodiment 1. A connection including a first profile having a first end and a first lumen, the first profile including a first polymeric material and a second profile having a second end and a second lumen, the second profile including a second polymeric material, a metal, or combination thereof, wherein the first end and the second end are coincidently welded via an ionized gas treatment.

Embodiment 2. A sterile connection including a first profile having a first end and a first lumen, the first profile including a first polymeric material and a second profile having a second end and a second lumen, the second profile including a second polymeric material, a metal, or combination thereof, wherein the first end and the second end are coincidently welded via an ionized gas treatment, wherein the ionized gas treatment provides a sterile connection between the first profile and the second profile.

Embodiment 3. A method of providing a sterile connection including: providing a first profile having a first end and a first lumen, the first profile including a first polymeric material; providing a second profile having a second end and a second lumen, the second profile including a second polymeric material, a metal, or combination thereof; providing an ionized gas treatment; and contacting the first end directly to the second end to coincidently weld the first end to the second end and provide a sterile connection between a treated surface of the first profile and a treated surface of the second profile.

Embodiment 4. The connection, sterile connection or method of providing the sterile connection of any of the preceding embodiments, wherein the first polymer material and the second polymeric material are the same polymeric material.

Embodiment 5. The connection, sterile connection or method of providing the sterile connection of any of the preceding embodiments, wherein the first polymeric material and the second polymeric material are different polymeric materials.

Embodiment 6. The connection, sterile connection or method of providing the sterile connection of any of the preceding embodiments, wherein the first polymeric material includes a thermoplastic elastomer, a thermoset elastomer, or combination thereof.

Embodiment 7. The connection, sterile connection or method of providing the sterile connection of embodiment 6, wherein the thermoplastic elastomer includes a polystyrene, a polyester, a silicone copolymer, a silicone thermoplastic vulcanizate, a copolyester, a polyamide, a fluoropolymer, a polyolefin, a polyether-ester copolymer, a thermoplastic urethane, a polyether amide block copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or combination thereof.

Embodiment 8. The connection, sterile connection or method of providing the sterile connection of embodiment 7, wherein the thermoset elastomer includes a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a blend, or combination thereof.

Embodiment 9. The connection, sterile connection or method of providing the sterile connection of any of the preceding embodiments, wherein the second polymeric material includes a thermoplastic elastomer, a thermoset elastomer, or combination thereof.

Embodiment 10. The connection, sterile connection or method of providing the sterile connection of embodiment 9, wherein the thermoplastic elastomer includes a polystyrene, a polyester, a silicone copolymer, a silicone thermoplastic vulcanizate, a copolyester, a polyamide, a fluoropolymer, a polyolefin, a polyether-ester copolymer, a thermoplastic urethane, a polyether amide block copolymer, a polyamide copolymer, a styrene block copolymer, a polycarbonate, a thermoplastic vulcanizate, an ionomer, a polyoxymethylene (POM), an acrylonitrile butadiene styrene (ABS), an acetal, an acrylic, a polyvinyl chloride (PVC), a blend, or combination thereof.

Embodiment 11. The connection, sterile connection or method of providing the sterile connection of embodiment 9, wherein the thermoset elastomer includes a silicone elastomer, a diene elastomer, a butyl rubber, a natural rubber, a polyurethane rubber, an ethylene propylene diene monomer rubber, an isoprene rubber, a nitrile rubber, a styrene butadiene rubber, a blend, or combination thereof.

Embodiment 12. The connection, sterile connection or method of providing the sterile connection of any of the preceding embodiments, wherein the first profile includes a silicone elastomer and the second profile includes a silicone elastomer.

Embodiment 13. The connection, sterile connection or method of providing the sterile connection of any of the preceding embodiments, wherein the first profile includes a silicone elastomer and the second profile includes a blend of a styrene block copolymer and a polyolefin.

Embodiment 14. The connection, sterile connection or method of providing the sterile connection of any of the preceding embodiments, wherein the profile includes a tubing, a port, a connector, a hose, a nozzle, a needle, or combination thereof.

Embodiment 15. The connection, sterile connection or method of providing the sterile connection of any of the preceding embodiments, wherein the coincidental weld is a circumferential seal.

Embodiment 16. The connection, sterile connection or method of providing the sterile connection of any of the preceding embodiments, wherein the first lumen, the second lumen, or combination thereof includes a plurality of lumen.

Embodiment 17. The connection, sterile connection or method of providing the sterile connection of any of the preceding embodiments, wherein the coincident weld withstands a seal integrity pressure test of at least 1 psi, such as at least 5 psi, such as at least 10 psi, such as at least 15 psi, or even at least 20 psi air pressure for about 30 minutes under dry and wet conditions.

Embodiment 18. The connection, sterile connection or method of providing the sterile connection of any of the preceding embodiments, wherein the ionized gas treatment includes corona treatment, ion treatment, plasma treatment, or combination thereof.

Embodiment 19. The connection, sterile connection or method of providing the sterile connection of embodiment 18, wherein the plasma treatment is provided for less than 2 minutes, such as less than 1 minute, such as less than 45 seconds, such as less than 30 seconds, or even less than 10 seconds.

Embodiment 20. The connection, sterile connection or method of providing the sterile connection of any of the preceding embodiments, wherein the first profile has a wall thickness of about 0.02 inches to about 4.0 inches, such as about 0.05 inches to about 1.0 inch, or even about 0.1 inches to about 0.375 inches.

Embodiment 21. The connection, sterile connection or method of providing the sterile connection of any of the preceding embodiments, wherein the second profile has a wall thickness of about 0.02 inches to about 4.0 inches, such as about 0.05 inches to about 1.0 inch, or even about 0.1 inches to about 0.375 inches.

Embodiment 22. The connection, sterile connection or method of providing the sterile connection of embodiments 20 and 21, wherein the first profile and the second profile have the same wall thicknesses.

Embodiment 23. The connection, sterile connection or method of providing the sterile connection of embodiments 20 and 21, wherein the first profile and the second profile have different wall thicknesses.

Embodiment 24. The connection, sterile connection or method of providing the sterile connection of any of the preceding embodiments, wherein the coincidental weld has a tensile strength between the first profile and the second profile of at least about 10 psi, such as at least about 50 psi, or even at least 300 psi.

Embodiment 25. The connection, sterile connection or method of providing the sterile connection of any of the preceding embodiments, wherein the profile is used for biopharm applications, FDA applications, medical applications, laboratory applications, or combination thereof.

Embodiment 26. The connection, sterile connection or method of providing the sterile connection of any of the preceding embodiments, wherein a fastening device surrounds at least a portion of an exterior seam of the coincidental weld.

Embodiment 27. The connection, sterile connection or method of providing the sterile connection of embodiment 26, wherein the fastening device includes a clamp, a polymer tape, an overmolded polymer, a glue, or combination thereof.

Embodiment 28. The connection, sterile connection or method of providing the sterile connection of embodiment 27, wherein the polymer tape includes a silicone tape.

Embodiment 29. The connection, sterile connection or method of providing the sterile connection of embodiment 28, wherein a surface of the silicone tape is exposed to an ionized gas treatment prior to adhesion to the exterior seam of the coincidental weld.

Embodiment 30. The connection of any of the preceding embodiments, wherein the ionized gas treatment provides a sterile connection of a treated surface of the first profile and a treated surface the second profile.

Embodiment 31. The connection, sterile connection or method of providing the sterile connection of any of the preceding embodiments, wherein the connection is used for biopharm applications, FDA applications, medical applications, laboratory applications, or combination thereof.

Embodiment 32. The connection, sterile connection or method of providing the sterile connection of any of the preceding embodiments, wherein the interface has a failure mode of adhesive failure.

Embodiment 33. The connection, sterile connection or method of providing the sterile connection of any of the preceding embodiments, having a surface tension at the interface of greater than about 20 mN/m, such as greater than about 22 mN/m, or even greater than about 25 mN/m.

Embodiment 34. The connection, sterile connection or method of providing the sterile connection of any of the preceding embodiments, having a surface tension at a treated surface of greater than about 20 mN/m, such as greater than about 22 mN/m, or even greater than about 25 mN/m.

Embodiment 35. The connection, sterile connection or method of providing the sterile connection of any of the preceding embodiments, having a surface tension increase at a treated interface for connection and/or treated surface for at least about 1 mN/m, at least about 3 mN/m, or even at least than about 10 mN/m.

Embodiment 36. The connection, sterile connection or method of providing the sterile connection of any of the preceding embodiments, wherein the interface is substantially free of any dynamic covalent chemistry.

Embodiment 37. The connection, sterile connection or method of providing the sterile connection of any of the preceding embodiments, further including a visible difference at the interface on a treated and/or bonded area versus non-treated and/or non-bonded area.

Embodiment 38. The connection, sterile connection or method of providing the sterile connection of any of the preceding embodiments, wherein an extraction profile of the first profile and the second profile before and after ionized gas treatment is identical.

Embodiment 39. The connection, sterile connection or method of providing the sterile connection of any of the preceding embodiments, wherein a change in particulates in the first profile and the second profile before and after ionized gas treatment is +/−5%, such as +/−15%, or even+/−50%.

Embodiment 40. The method of providing the sterile connection of embodiments 3-39, further including disconnecting the coincident weld; providing an additional ionized gas treatment; and contacting the first end directly to the second end to coincidently bond the first end to the second end at the interface.

The concepts described herein will be further described in the following examples, which do not limit the scope of the disclosure described in the claims. The following examples are provided to better disclose and teach processes and compositions of the present invention. They are for illustrative purposes only, and it must be acknowledged that minor variations and changes can be made without materially affecting the spirit and scope of the invention as recited in the claims that follow.

EXAMPLES

General Procedure for Welding and Burst Test:

Welding: place the two tubes under plasma, exposure the cross-sections to plasma for a certain time; then immediately after the treatment, align the tubes and "weld" them by applying gentle compression force (less than 100N but making sure the ends are in full contact).

Post treatment of tubing: the welded tubing are stored in ambient temperature and pressure for certain period before connecting to compression air for burst pressure test.

Burst Test Pressure Procedure

The pressure is provided via connecting to a compression air line with a regulator to control the pressure during the test. One end of the tested "welded" tubing is connected to the regulator using braid reinforcing silicone tubing with proper fitting. The other end of the "welded" tubing is connected to a pressure gauge. The whole tubing is immersed in water during the test. The fail of the tubing (burst at the joint or burst of tubing) can be easily indicated by the air bubble in the water tank. When test begins, the pressure is increased by controlling the regulator with the rate about 2 psi/s. The highest pressure during the test is record. The whole process is also recorded by video and confirmed all the reading is correct after test.

Standard Operating Procedure of the Test:

1. Connect the welded tubing to the test apparatus.

2. Lay the pressure testing apparatus on a flat surface.

3. Fill the water tank with enough water to submerge test specimens.

4. Connect pressure testing apparatus to a clean, dry compressed air supply.

5. Determine the correct multi-barb fitting sizes for the tubing to be tested. Slightly oversized barbed fittings are acceptable as long as they do not cause the tubing to leak at the barbed fitting.

6. Install both end of the specimen on to the barbed fitting and secure with at least 1 zip ties. [00101]7. Slowly pressurize the apparatus (~2 psi/s) until air bubbles were observed in the water tank.

8. Clean and dry the apparatus to repeat the test as necessary, in general, at least 3 samples are tested for one condition.

Two Different Burst Types are Recorded:

1) Where the tube inflates with the increase of the pressure from the compression air, and burst at the joint at the highest pressure (named here as Type A burst).

2) Where the tubing inflates with the increase of the pressure from the compression air, and then the tubing materials yield, the tubing bulges; however the pressure drops, then tubing break at the joint, the burst pressure is lower than the highest pressure during the test (named here as Type B burst).

Test 1:

Materials: 50 shore A durometer silicone tubing "welding" with same 50 shore A durometer silicone tubing (½ inch ID, ¾ inch OD). Results can be seen in Table 1.

TABLE 1

| | Plasma treatment time (seconds) | Storage time at ambient condition | Highest pressure during test (psi) | Burst type |
|---|---|---|---|---|
| 1-1* | 5 | 1 minute | 25 | A |
| 1-2* | 5 | 3 minute | 25 | A |
| 1-3* | 5 | 5 minute | 31.5 | A |
| 1-4* | 5 | 15 minute | 32 | A |
| 1-5 | 5 | 2 hour | 34.6 ± 0.6 | A |
| 1-6# | 5 | 2 hour | 38 | B |
| 1-7* | 5 | 2 days | 34 | A |

TABLE 1-continued

|  | Plasma treatment time (seconds) | Storage time at ambient condition | Highest pressure during test (psi) | Burst type |
|---|---|---|---|---|
| 1-8 | 10 | 2 hour | 32.8 ± 0.9 | A |
| 1-9 | 15 | 2 hour | 31.3 ± 1 | A |
| 1-10 (control)* | — | — | 40.5 | A |

*Only one sample is tested at this condition. For the rest of the tests, at least 2 samples are tested.
The coincident weld is reinforced with a layer of silicone tape (wrapping with plasma induced adhesion).

Test 2:

The following materials are tested: A 65 shore A durometer silicone tubing "welding" with the same 65 shore A durometer silicone tubing (½ inch ID, ¾ inch OD). Results can be seen in Table 2.

TABLE 2

|  | Plasma treatment time (s) | Storage time at ambient condition | Highest pressure during test (psi) | Burst type |
|---|---|---|---|---|
| 2-1* | 5 | 2 h | 50.5 | A |
| 2-2*# | 5 | 2 h | 49 | B |
| 2-3 (control)* | — | — | 66 | A |

*Only one sample is tested at this condition. For the rest of the tests, at least 3 samples are tested.
The joint is reinforced with a layer of silicone tape (wrapping with plasma induced adhesion).

Test 3:

The following materials are tested: a silicone tubing "welding" with C-Flex tubing (½ inch ID, ¾ inch OD). Shore A durometer of the silicone tubing is seen in Table 3. Results can be seen in Table 3.

TABLE 3

|  | Silicone hardness | Plasma treatment time at silicone (seconds) | Plasma treatment time at C-Flex (seconds) | Storage time at ambient condition | Highest pressure during test (psi) | Burst type |
|---|---|---|---|---|---|---|
| 3-1* | 50 | 5 | 5 | 2 hour | 23 | A |
| 3-2* | 50 | 5 | 15 | 2 hour | 21.5 | A |
| 3-3*# | 65 | 5 | 50 | 2 hour | 45 | A |

*Only one sample is tested at this condition. For the rest of the tests, at least 3 samples are tested.
The joint is reinforced with a layer of silicone tape (wrapping with plasma induced adhesion).

Tensile Test—Non-ASTM Standard

Plasma treatment conditions are in Table 4 along with max strain, tensile strength, and young's modulus measured by the following procedure.

Preparation of the sample: for the as-is tubing/control, the tubing is cut with a length ~4-5 inch; for welded tubing, the tubing after welding is ~4-5 inch with the welding line locating at the middle.

Place the tubing in the Instron tensile test machine with both ends into grips. The gas between the grips is set at 2 inch, making sure the grips are securely holding the tubing sample.

Pull the sample with the tensile machine at a rate of 20 in/min until tubing break, the grips are pulled to 20 inches apart, or until the maxima tensile range of the machine is reached.

Remove the sample from the tensile machine and inspect for visual failure. Calculate the strength based on the ring area of tubing cross-section.

All durometer is shore A. Control samples are tubes un-cut tubes.

TABLE 4

|  | Tubing A | Tubing B | Plasma treatment time at A tubing (sec.) | Plasma treatment time at B tubing (sec.) | Max strain (%) | Max tensile strength (psi) |
|---|---|---|---|---|---|---|
| 1 | 50 duro silicone | C-Flex #1 | 5 | 20 | 43 ± 2 | 134 ± 5 |
| 2* | 65 duro silicone | C-Flex #1 | 5 | 20 | 22 | 106 |
| 3* | 50 duro silicone | C-Flex #1 | 5 | 35 | 45 | 133 |
| 4* | 65 duro silicone | C-Flex #1 | 5 | 35 | 28 | 127 |
| 5* | 65 duro silicone | C-Flex #1 | 5 | 50 | 48 | 103 |
| 6 | 65 duro silicone | 65 duro silicone | 5 | 5 | 25 ± 2 | 112 ± 8 |
| 7# | 65 duro silicone | 65 duro silicone | 5 | 5 | 73 ± 50 | 215 ± 84 |
| 8 | 50 duro silicone | 50 duro silicone | 5 | 5 | 47 ± 6 | 116±11 |
| 9# | 50 duro silicone | 50 duro silicone | 5 | 5 | 283 ± 32 | 345 ± 38 |
| 10& |  | 50 duro silicone control |  |  | >581 ± 60 | >581 ± 50 |
| 11& |  | 65 duro silicone control |  |  | >811 ± 8 | >893 ± 4 |
| 12 |  | C-Flex #1 control |  |  | >1332 | >824 |
| 13 |  | C-Flex #1 thermal welding |  |  | 98 | 266 |
| 14 | C-Flex #1 | C-Flex #1 | 60 | 60 | 35 | 137 |

TABLE 4-continued

| | Tubing A | Tubing B | Plasma treatment time at A tubing (sec.) | Plasma treatment time at B tubing (sec.) | Max strain (%) | Max tensile strength (psi) |
|---|---|---|---|---|---|---|
| 15 | | C-Flex #2 control | | | | |
| 16 | | C-Flex #2 thermal welding | | | 520 | 2510 |
| 17 | C-Flex #2 | C-Flex #2 | 60 | 60 | 35 | 40 |

*Only one sample is tested at this condition. For the tests of rest condition, at least 3 samples are tested.
The joint is reinforced with a layer of silicone tape (wrapping with plasma induced adhesion).
&The control sample did not break in the middle of the tubing, test terminated either when sample slips from clamps or breaks from the defect due to clamping.

The same tensile test conditions are used to determine the tear strength and mechanical strength. Results for tear strength can be seen in Table 5.

TABLE 5

| | 65 duro Silicone Control Uncut tube | 65 duro Silicone plasma welded to 65 duro Silicone |
|---|---|---|
| Tear strength (ppi) | 897 | 281 |

Burst Pressure Test—Impact of Processing Parameter:

Materials: 50 duro silicone tubing "welding" with same 50 duro silicone tubing (½ inch ID, ¾ inch OD)

Burst pressure tests are performed with at least 2 hours after welding. Results can be seen in Table 6.

TABLE 6

| | | Argon flow (SLPM) | | |
|---|---|---|---|---|
| Burst pressure (psi) | | 2.8-3.0 | 6.0-6.3 | 15.0-15.3 |
| Treatment time (s) | 5 | 29.6 ± 1.7 | 32.3 ± 0.4 | 18.3 ± 5.5 |
| | 10 | 34.6 ± 0.6 | 32.8 ± 0.9 | 31.3 ± 1 |
| | 15 | 33.3 ± 1.7 | 33.6 ± 1 | 29.3 ± 0.9 |

Surface tension is tested via the following conditions:

Plasma welding surface energy of C-Flex and silicone tubing after exposure to plasma for welding procedure conditions and results are as follows.

Description of the tested materials is seen in Table 7.

TABLE 7

| Reference | Description |
|---|---|
| C-flex control | Control C-flex sample (no plasma) |
| C-flex plasma weld | C-flex, adjacent to plasma weld mark |
| Silicone control | Control silicone samples (no plasma) |
| Silicone plasma weld | Silicone, adjacent to plasma weld mark |

ASTM D7334-08, "Standard Practice for Surface Wettability of Coatings, Substrates and Pigments by Advancing Contact Angle Measurement" is followed. This practice deals with the measuring of contact angles to characterize the wettability of surfaces. Two different solvents are used: water and diiodomethane (MI).

The instrument used is a Kruss Mobile Surface Analyzer, which uses an automatic liquid dispenser to place drops of solvent (volume=~1 µL) on a sample. Drops of water and MI are placed in parallel and allowed to settle on the surface. The values of the two contact angles are determined using drop shape analysis. 5+ drops of each solvent are tested on each sample surface.

For analysis, the Owens-Wendt method is used, which utilizes both the dispersive and polar components of each solvent to determine the surface energy components of the samples. The equation for the method follows:

$$\frac{\sigma_L(\cos\theta + 1)}{2\sqrt{\sigma_L^D}} = \frac{\sqrt{\sigma_S^P}\sqrt{\sigma_L^P}}{\sqrt{\sigma_L^D}} + \sqrt{\sigma_S^D}$$

Where cos θ: Cosine of the contact angle of the liquid drop on the sample;

Surface tension of the liquid;

$\sigma_L$: Dispersive component of the surface tension of the liquid;

$\sigma_L^D$: Polar component of the surface tension of the liquid;

$\sigma_S^D$: Dispersive component of the surface energy of the sample;

$\sigma_S^P$: Polar component of the surface energy of the sample.

The equation fits a linear equation y=mx+b. By fitting a linear regression using the mean contact angle of each drop and liquid surface tension components, the surface energy components of the sample is determined.

Contact angle measurements and surface energy calculations are shown in Table 8, Table 9, Table 10, and Table 11 below:

TABLE 8

Contact angle measurements of control samples

| | Measurement | | | |
|---|---|---|---|---|
| Sample ID | Mean Water CA (°) | STD | Mean MI CA (°) | STD |
| C-flex control | 100.4 | 2.6 | 56.8 | 8.8 |
| Silicone control | 101.6 | 5.7 | 98.5 | 3.6 |

TABLE 9

Contact angle measurement over time

| Sample Measurement ID | Mean Water CA (°) | | | Mean MI CA (°) | | |
|---|---|---|---|---|---|---|
| | Days after plasma treatment | | | | | |
| | 0 | 68 | 131 | 0 | 68 | 131 |
| C-flex plasma weld | 72.4 ± 13.2 | 69.6 ± 9.3 | 88.1 ± 4.8 | 44.3 ± 6.1 | 44.5 ± 5.7 | 43.9 ± 5.5 |
| Silicone plasma weld | 93.9 ± 6.5 | 95.1 ± 8.2 | 89.5 ± 4.6 | 73.0 ± 3.8 | 72.8 ± 12.8 | 65.9 ± 6.3 |

TABLE 10

Surface energy calculations

| Sample Surface Energy ID | Surface Free Energy [mN/m] | STD | Dispersive [mN/m] | STD | Polar [mN/m] | STD |
|---|---|---|---|---|---|---|
| C-flex control | 30.8 | 5.5 | 30.4 | 5.0 | 0.3 | 0.4 |
| Silicone control | 13.6 | 3.5 | 9.2 | 1.3 | 4.4 | 2.2 |

TABLE 11

Surface energy calculations

| Sample Surface Energy ID | Surface Free Energy [mN/m] | | | Dispersive [mN/m] | | | Polar [mN/m] | | |
|---|---|---|---|---|---|---|---|---|---|
| | Days after plasma treatment | | | | | | | | |
| | 0 | 68 | 131 | 0 | 68 | 131 | 0 | 68 | 131 |
| C-flex plasma weld | 44.4 ± 9.3 | 45.6 ± 7.6 | 39.2 ± 4.1 | 37.4 ± 3.3 | 37.3 ± 3.0 | 37.6 ± 2.9 | 7.0 ± 6.0 | 8.3 ± 4.5 | 1.6 ± 1.1 |
| Silicone plasma weld | 24.3 ± 4.2 | 22.1 ± 9.9 | 28.7 ± 5.4 | 21.2 ± 2.1 | 18.9 ± 6.7 | 25.2 ± 3.6 | 3.0 ± 2.1 | 3.2 ± 3.2 | 3.5 ± 1.8 |

With the silicone plasma weld, using a Sharpie permanent marker, the surface tension is tested. Before the treatment, the surface is not wettable. After the treatment, the surface is wettable.

Peel test conditions are as follows:

The adhesion strength is measured by the following procedure. Preparation of the sample: Two silicone slabs with ~1/16 inch thick are stacked and welded by plasma. The welded silicone slabs is cut into ¼ inch wide pieces. The welded slabs are then placed in the instron with each slab gripped, and peeled with T shape/180 degree peel. The peel force is 9.9±3.9 ppi.

Extraction profile is determined as follows: The control silicone tubing and welded silicone tubing are extracted using 50% water and 50% of ethanol for 24 hours at 70° C. Then Gas Chromatograph/Mass Spectrometry is used to analyze the extraction profile. Notably, plasma welding does not substantially change the extraction profile of a material, such as silicone tubing. In an example, when comparing a silicone control and a plasma welded silicone, plasma welding does not increase the extraction of siloxanes.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A connection comprising a first profile having a first end and a first lumen, the first profile comprising a first polymeric material comprising a thermoset silicone elastomer material and a second profile having a second end and a second lumen, the second profile comprising a second thermoset silicone elastomer material, wherein the first end and the second end are coincidently welded at an interface via an ionized gas treatment to form a sterile coincidental weld.

2. The connection in accordance with claim 1, wherein the first silicone elastomer thermoset material and the second silicone elastomer thermoset material comprises a silicone matrix material wherein the first silicone elastomer thermoset material and the second silicone elastomer thermoset material are the same silicone matrix material.

3. The connection in accordance with claim 1, wherein the first silicone elastomer thermoset material and the second silicone elastomer thermoset material comprises a silicone matrix material wherein the first silicone elastomer thermoset material and the second silicone elastomer thermoset material are different silicone matrix materials.

4. The connection in accordance with claim 1, wherein the first polymeric material of the first profile consists essentially of the thermoset silicone elastomer material.

5. The connection in accordance with claim 1, wherein the second profile consists essentially of the thermoset silicone elastomer material.

6. The connection in accordance with claim 1, wherein the first profile comprises a first tube and the second profile comprises a second tube.

7. The connection in accordance with claim 1, wherein the first profile comprises a tubing, a port, a connector, a hose, a needle, a nozzle, or combination thereof.

8. The connection in accordance with claim 1, wherein the coincidental weld is a circumferential seal.

9. The connection in accordance with claim 1, wherein the coincident weld withstands a seal integrity pressure test of at least 1 psi, such as at least 5 psi, such as at least 10 psi, such as at least 15 psi, or even at least 20 psi air pressure for about 30 minutes under dry and wet conditions.

10. The connection in accordance with claim 1, wherein the first profile and the second profile have the same wall thicknesses.

11. The connection in accordance with claim 1, wherein the first profile and the second profile have different wall thicknesses.

12. The connection in accordance with claim 1, wherein the coincidental weld has a tensile strength between the first profile and the second profile of at least about 10 psi, such as at least about 50 psi, or even at least 300 psi.

13. The connection in accordance with claim 1, wherein the first profile has a wall thickness of about 0.02 inches to about 4.0 inches.

14. The connection in accordance with claim 1, wherein the second profile has a wall thickness of about 0.02 inches to about 4.0 inches.

15. The connection in accordance with claim 1, wherein the interface has a surface tension of greater than about 20 mN/m.

16. The connection in accordance with claim 1, wherein the second profile comprises a tubing, a port, a connector, a hose, a needle, a nozzle, or combination thereof.

17. A sterile connection comprising a first tube having a first end and a first lumen, the first tube comprising a first polymeric material comprising a thermoset silicone elastomer and a second tube having a second end and a second lumen, the second tube comprising a thermoset silicone elastomer material, wherein the first end and the second end are coincidently welded at an interface via an ionized gas treatment, wherein the ionized gas treatment provides a sterile coincidental weld between the first tube and the second tube.

* * * * *